United States Patent [19]

Bell

[11] 4,068,125
[45] Jan. 10, 1978

[54] LASER ABSORPTION SPECTROSCOPY EMPLOYING VARYING ABSORPTION CONDITIONS

[75] Inventor: William E. Bell, Mountain View, Calif.

[73] Assignee: Diax Corporation, Los Altos Hills, Calif.

[21] Appl. No.: 550,519

[22] Filed: Feb. 18, 1975

[51] Int. Cl.² .............................. G01J 1/00; G01J 3/30
[52] U.S. Cl. ..................................... 250/340; 250/343; 356/73; 356/85
[58] Field of Search ...................... 356/85, 86, 96, 97, 356/93, 73, 51; 250/338, 339, 340, 341, 343

[56] References Cited

U.S. PATENT DOCUMENTS

| | | | |
|---|---|---|---|
| 3,032,654 | 5/1962 | Fay et al. | 356/86 |
| 3,289,026 | 11/1966 | Elton | 356/86 |
| 3,354,315 | 11/1967 | Preston et al. | 356/85 |
| 3,521,958 | 7/1970 | Treharine | 356/93 |
| 3,749,495 | 7/1973 | Wilkins et al. | 356/85 |
| 3,790,282 | 2/1974 | Fielding | 356/86 |
| 3,809,479 | 5/1974 | Whelan et al. | 356/86 |
| 3,811,777 | 5/1974 | Chance | 356/85 |
| 3,820,901 | 6/1974 | Kreuzer | 356/97 |
| 3,836,255 | 9/1974 | Schuman | 356/85 |
| 3,972,627 | 8/1976 | Rabl et al. | 356/246 |

Primary Examiner—Vincent P. McGraw
Attorney, Agent, or Firm—Lowhurst & Aine

[57] ABSTRACT

In laser absorption spectroscopy a fluid sample is irradiated with a beam of coherent optical radiation preferably in the infrared band. A detector such as an acoustic detector or thermal detector is coupled in acoustic or thermal energy exchanging relation, respectively, with the fluid medium to detect the absorption of energy, if any, by the fluid from the beam of coherent radiation. One or more of the physical or chemical parameters of the fluid or substances interacting with the fluid are changed and resultant changes, if any, are detected in the absorption of energy by the fluid to yield information concerning the fluid or substances interacting with the fluid.

10 Claims, 9 Drawing Figures

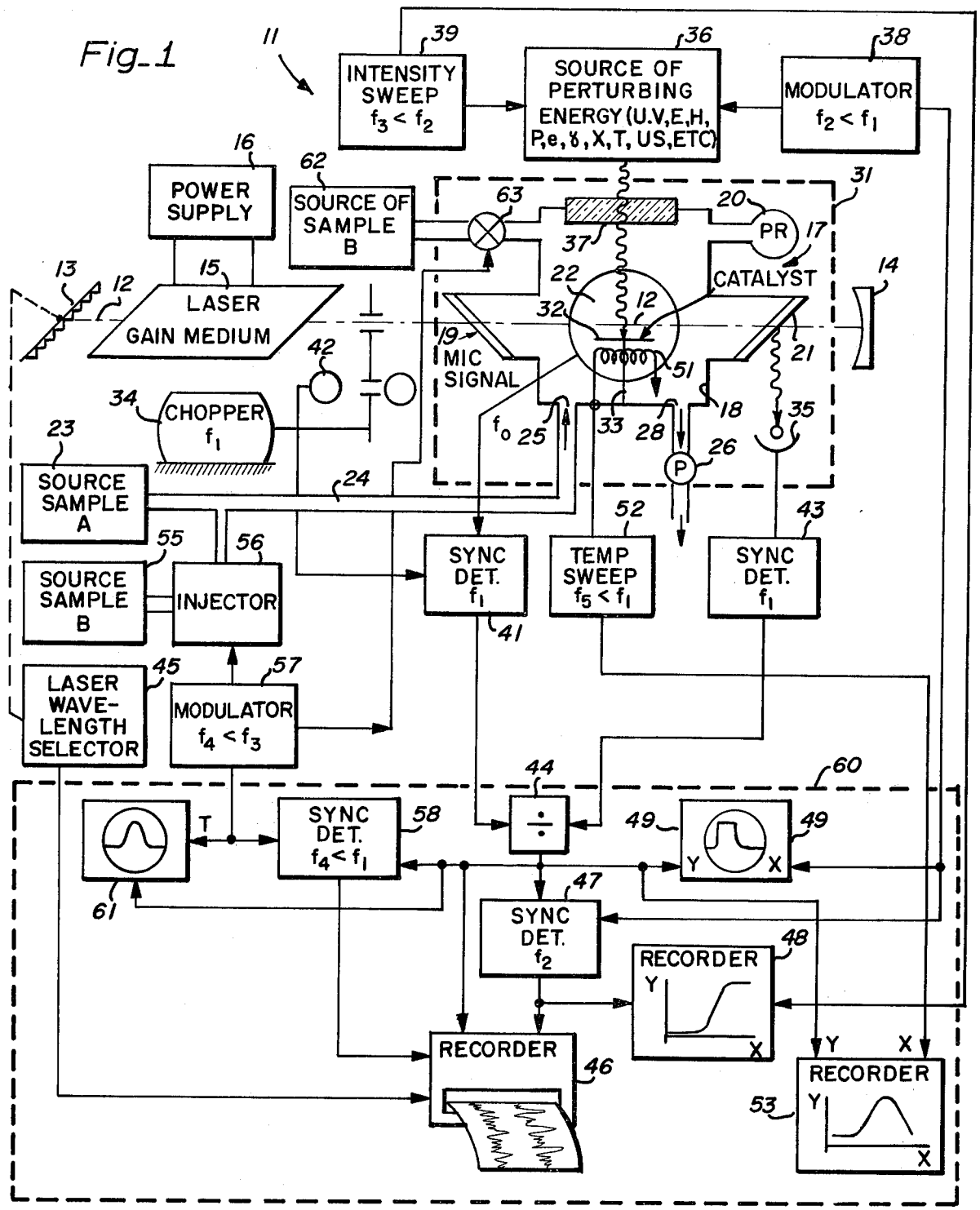
Fig_1

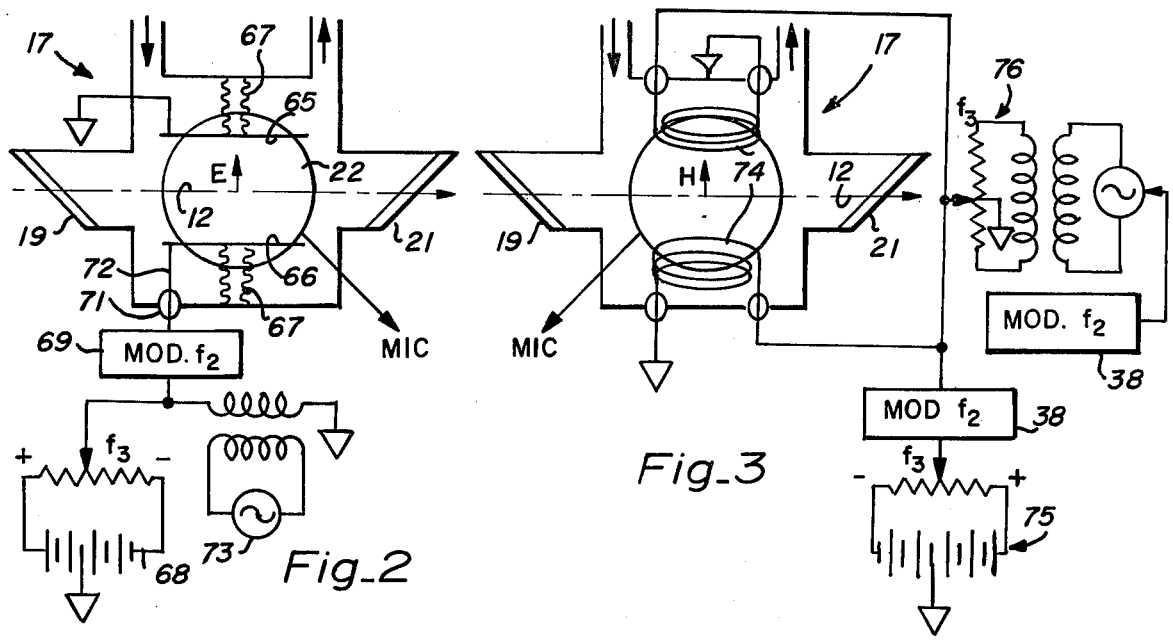
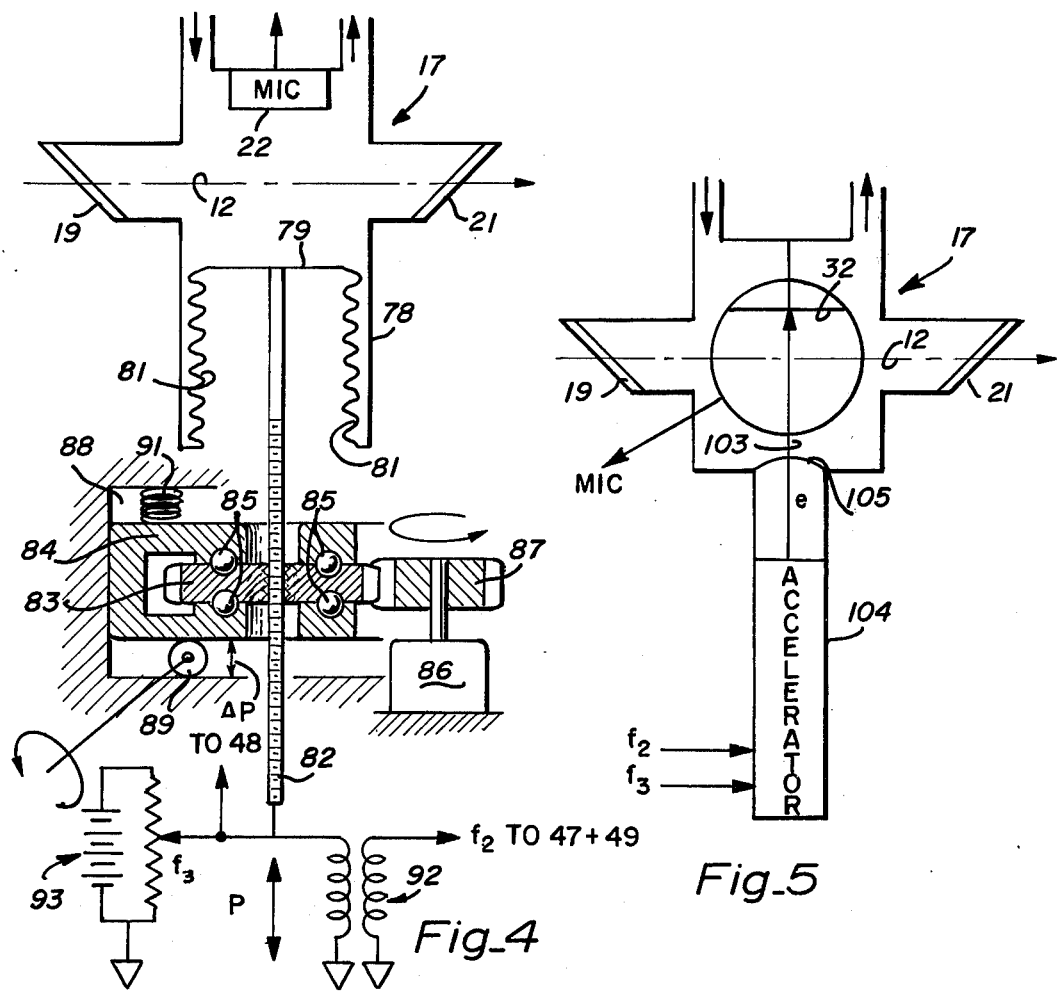

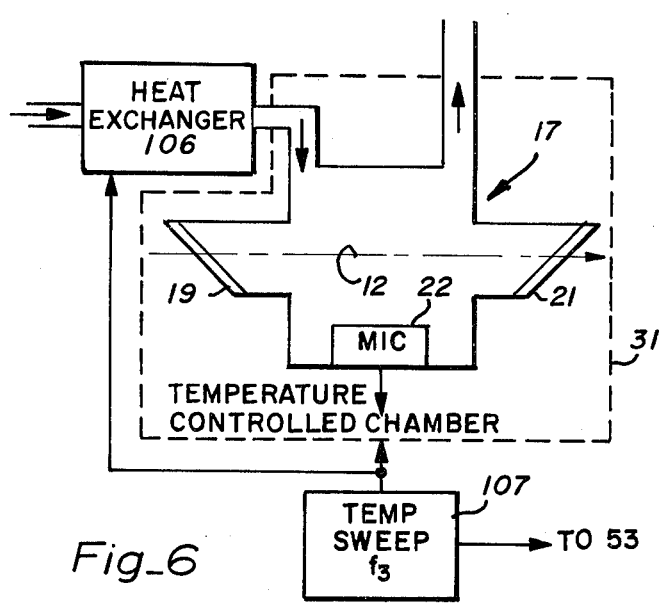
Fig_6
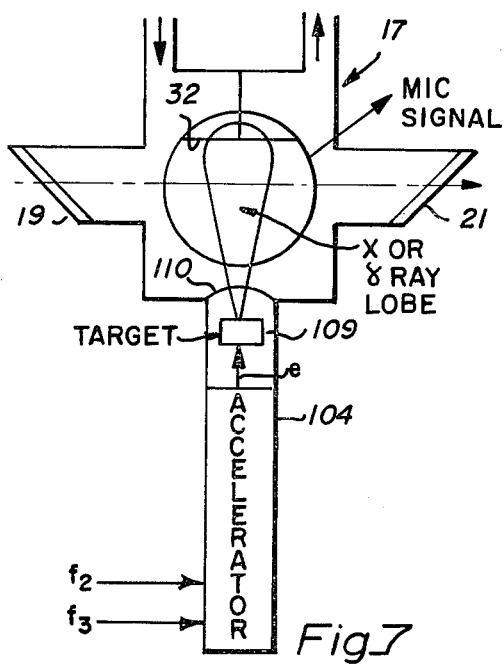
Fig_7
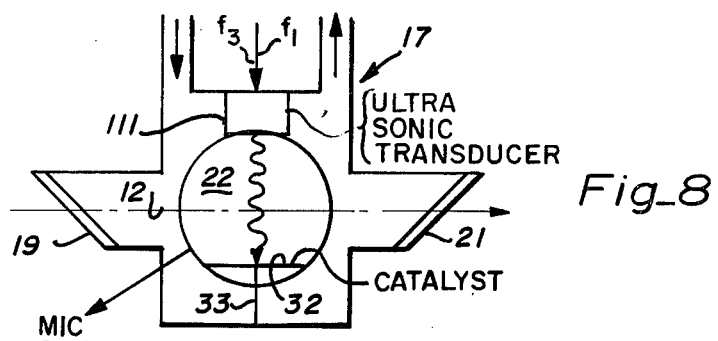
Fig_8
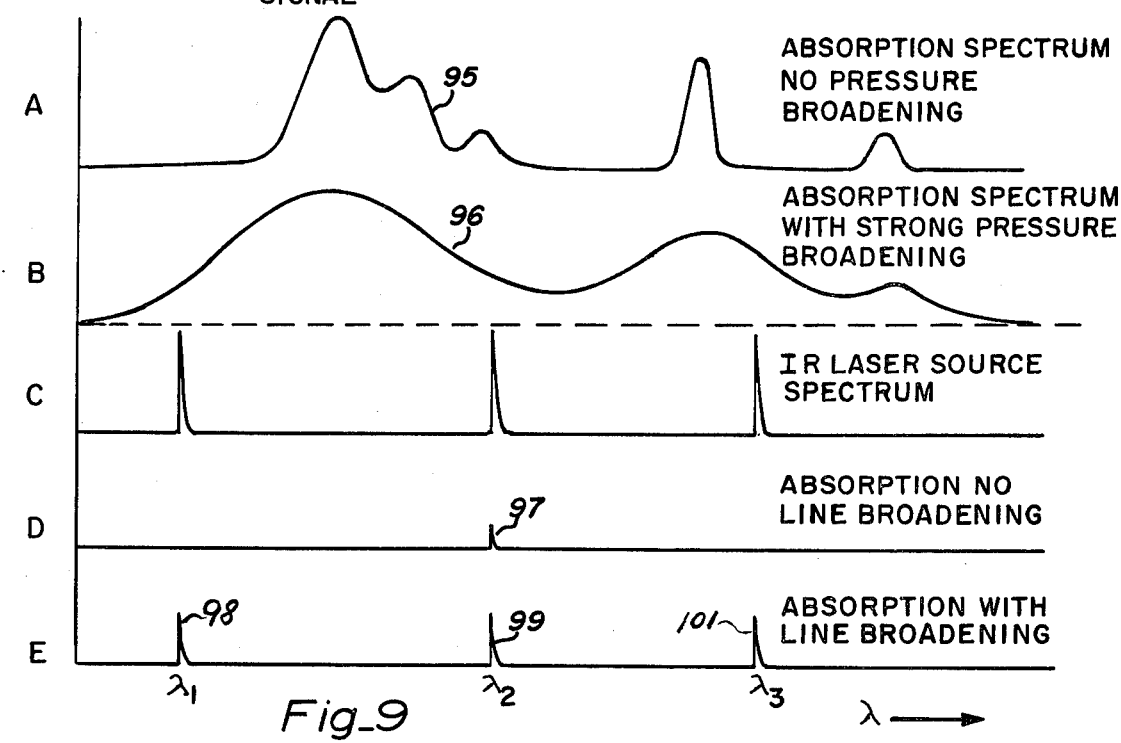
Fig_9

LASER ABSORPTION SPECTROSCOPY EMPLOYING VARYING ABSORPTION CONDITIONS

BACKGROUND OF THE INVENTION

The present invention relates in general to laser absorption spectroscopy and more particularly to such spectroscopy wherein a laser beam of infrared energy irradiates a fluid sample and means are provided for detecting the absorption of infrared energy by the sample from the laser beam.

DESCRIPTION OF THE PRIOR ART

Heretofore, infrared laser absorption spectroscopy has employed an optoacoustic sample detection cell for analyzing fluid samples and, in particular, for detecting certain pollutants in the air to concentration levels as low as parts per billion. Such a laser spectrometer is disclosed in: U.S. Pat. No. 3,820,901 issued June 28, 1974; in an article titled "Laser Optoacoustic Spectroscopy: A New Technique of Gas Analysis" appearing in *Analytical Chemistry*, Vol. 46, No. 2 of February 1974, pages 239–244; in *Science*, Vol. 177, pages 347–349 of July 28, 1972 in an article titled "Air Pollution: Sensitive Detection of Ten Pollutant Gases by Carbon Monoxide and Carbon Dioxide Lasers"; and in U.S. Pat. No. 3,659,452, issued May 2, 1972.

In these prior art laser absorption spectrometers, the laser, which is preferably a relatively high power output carbon dioxide or carbon monoxide laser, produces an output laser beam which is tunable to selected wavelengths within a band of infrared wavelengths of interest, i.e., the band of wavelengths over which certain gaseous sample constituents are known to have infrared absorption spectra. The laser output beam is directed through an optoacoustic cell containing the gaseous material to be analyzed. A sensitive microphone is coupled to the gaseous sample inside the sample cell. The laser beam is chopped at a certain chopping frequency, as of 25 Hertz, to produce a corresponding modulation of the absorption, if any, of the laser beam energy by the sample gas under analysis. Absorption of energy from the laser beam by the gas produces heating thereof which results in generating an acoustic wave which is detected by the microphone. The detected signal is processed to produce an output signal as a function of the wavelength of the infrared energy of the tunable laser beam to derive an absorption spectrum of or absorption spectral data concerning the sample under analysis.

While these prior art laser absorption spectrometers provide useful information concerning the absorption spectra of various molecules it would be desirable to employ laser absorption spectroscopy for analyzing and providing useful information concerning the magnetic and electric polarization of the molecules, their dissociation and recombination rates, transient molecular species in the case of reactions or interactions with other molecules or solid surfaces such as catalysts, catalyst behavior and/or mechanisms, suppression of interfering molecular species in the case of molecular reactions or interactions and enhancement of certain selected molecular species. Much of the aforementioned information can be obtained by perturbing the physical or chemical parameters of the fluid under analysis and observing the accompanying resultant changes in the absorption of the laser energy by the fluid under analysis.

SUMMARY OF THE PRESENT INVENTION

The principal object of the present invention is the provision of improved laser absorption spectroscopy.

In one feature of the present invention, the fluid sample medium under analysis has one or more of its physical or chemical parameters changed and resultant accompanying changes, if any, in the absorption of energy by the fluid medium are detected to yield useful information concerning the physical or chemical properties of the fluid under analysis.

In another feature of the present invention, the physical or chemical parameters of the fluid medium which are changed are selected from the group consisting of ion density, electron density, electric polarization, magnetic polarization, pressure, temperature, and molecular or atomic composition of the fluid.

In another feature of the present invention, the fluid medium under analysis is interacted with a solid medium and one or more physical or chemical parameters affecting the interaction of the fluid medium with the solid medium are changed and accompanying changes in the absorption of energy by the fluid medium from the probing beam of coherent optical radiation is detected to yield useful information concerning the interaction process.

In another feature of the present invention, the physical or chemical parameter of the fluid medium which is changed is changed at first and second rates, the second rate being higher than the first, and the accompanying changes in the absorption of energy at the first and second rates by the sample fluid medium from a probing beam of coherent radiation are detected.

In another feature of the present invention one or more of the physical or chemical parameters affecting interaction of the fluid medium with another medium such as a catalyst are changed to produce a resultant change in the absorption of energy by the fluid medium, such resultant change being detected as a function of time to derive information concerning the transient changes in the characteristics of the fluid sample under analysis.

In another feature of the present invention, the fluid under analysis is pressurized sufficiently to effect a substantial pressure broadening of the absorption spectrum of the sample under analysis. The resultant pressure broadened absorption of the sample under analysis is then detected at a plurality of wavelengths to derive absorption spectral data concerning the fluid under analysis.

In another feature of the present invention, the pressure of the fluid under analysis is modulated and the changes in absorption of the fluid from the laser beam at the pressure modulation frequency or harmonics thereof is detected to derive data concerning the slope of the absorption spectrum at the wavelength of the laser beam.

Other features and advantages of the present invention will become apparent from a perusal of the following specification taken in connection with the accompanying drawings wherein:

DESCRIPTION OF THE DRAWINGS

FIG. 1 is a schematic line diagram, partly in block diagram form, of a laser absorption spectrometer incorporating features of the present invention, FIG. 2 is a schematic line diagram of an alternative absorption detection cell of the present invention, FIG. 3 is a schematic line diagram of an alternative absorption detection cell of the present invention, FIG. 4 is a schematic line diagram of an alternative absorption detection cell employing pressure fluctuations, FIG. 5 is a schematic line diagram of an alternative absorption detection cell employing electron beam irradiation, FIG. 6 is a schematic line diagram of an alternative embodiment of an absorption detection cell employing temperature modulation, FIG. 7 is a schematic line diagram of an alternative absorption detection cell of the present invention incorporating means for irradiating the sample cell with X- or $\gamma$-ray radiation, FIG. 8 is a schematic line diagram of an alternative absorption detection cell of the present invention employing ultrasonic irradiation of the sample or interaction surfaces, and FIG. 9 is a composite spectral plot in (A) and (B) of a fluid under analysis with and without pressure broadening and including in (C) the irradiating infrared laser spectrum and in (D) and (E) the resultant detected absorption signals with and without pressure broadening.

DESCRIPTION OF THE PREFERRED EMBODIMENTS

Referring now to FIG. 1, there is shown a laser absorption spectrometer 11 incorporating features of the present invention. The spectrometer 11 includes a laser cavity (optical resonator) defined by the beam path 12 between a diffraction grating 13 and a totally reflective mirror 14. The laser gain medium, such as carbon monoxide, carbon dioxide, or helium-neon, is contained within a suitable envelope 15 and excited to produce stimulated emission of coherent radiation by means of an electrical discharge supplied with voltage and current from a power supply 16. At an optical wavelength corresponding to a resonance of the optical resonator and to a laser line of the laser gain medium, the optical resonator is excited to produce a coherent beam of optical radiation therein along the beam path 12.

In a typical example, the laser gain medium is chosen and the resonator is dimensioned so as to provide a laser beam of infrared wavelength that may be selected or tuned over a predetermined band of laser wavelengths of interest such as from 1.0 microns to 10 microns. Within this tunable band the laser will lase on a number of lines spaced in wavelength over the infrared band of interest.

A sample absorption detection cell 17 is disposed in the beam path for containing a fluid sample to be analyzed. The sample cell 17 includes a chamber 18 having a pair of Brewster angle windows 19 and 21 on opposite sides thereof in axial alignment with the laser beam path 12 for passage of the laser beam 12 through the detector cell 17. A microphone 22 is disposed within the cell in acoustic wave energy exchanging relation with the fluid medium therein to be analyzed. A source 23 of sample fluid to be analyzed, such as a gaseous hydrocarbon, having an infrared absorption spectrum is fed from the source 23 to the detector cell 17 via a suitable conduit 24 and inlet port 25. The fluid to be analyzed is either continuously or intermittently drawn through the cell 17 via a suitable gas pump 26 connected to the cell 17 via outlet port 28. A suitable pressure regulator 20, is connected in fluid communication with the cell 17 for controlling the pressure therein and an oven 31 surrounds the cell 17 for controlling the temperature thereof.

A catalytic material 32 is disposed in the cell 17 adjacent the laser beam path 12, such catalyst being supported from the wall of the cell via a pedestal 33. A beam chopper 34 is disposed in the beam path 12 for chopping the laser beam at a convenient modulation frequency, as of 1 to 400 Hertz. The Brewster window 21 of the cell 17 is slightly skewed relative to the Brewster angle for reflecting a certain small percentage of the beam power to a beam power detector 35.

A source 36 of perturbing energy, such as ultraviolet radiation, electric field, magnetic field, pressure, electron irradiation, $\gamma$ or X-ray radiation, heat or ultrasonic energy, is arranged in energy exchanging relation with the fluid medium within the cells 17 or with the catalytic surface 32 for changing a physical or chemical parameter of the fluid or of the interaction between the catalytic surface and the fluid to produce a resultant change in the absorption of the energy by the fluid sample from the beam 12. In the particular example illustrated in FIG. 1, the source 36 of perturbing energy is ultraviolet radiation which is passed into the cell 17 through an ultraviolet transmissive window 37 for irradiating both the fluid sample medium and the catalytic surface 32. The ultraviolet radiation produces photoelectrons on the catalytic surface 32 which interact with the fluid medium adjacent the surface 32 to produce a change in the absorption spectrum of the fluid under analysis. In addition, the radiation when of sufficient intensity will produce dissociation of the fluid medium, thereby altering the absorption spectrum. The source 36 of perturbing energy is modulated by modulator 3B at a first frequency $f_2$ which is less than the chopper frequency $f_1$. The modulator 3B, in a preferred embodiment, is a pulse modulator. In addition, the source 36 of perturbing radiation has its intensity modulated or swept by sweeper 39 at a second frequency $f_3$ which is less than $f_2$. In this manner, the energy density of the ultraviolet radiation as passed into the cell 17 can be modulated or varied for determining threshold values.

In operation, the chopped laser beam 12 of a selected wavelength is passed through the detection cell 17 and through the sample fluid medium along the beam path 12 adjacent the catalytic surface 32. The beam 12 is chopped at the chopping frequency $f_1$. Absorption of energy by the fluid medium from the beam 12 produces heating of the sample fluid medium at the chopper frequency $f_1$ thereby resulting in an acoustic wave at the chopper frequency which is detected by the microphone 22 and the detected signal is thence fed to one input of a synchronous detector 41 for synchronous detection against a sample of the chopping frequency derived from a detector 42 which detects a light beam passing through the chopper wheel so as to be chopped at the same frequency as the laser beam. The output of the synchronous detector 41 is an absorption signal corresponding to the absorption of energy by the fluid medium in the cell 17.

The beam power is detected in beam power detector 35 and the detected signal is fed to one input of a synchronous detector 43 for synchronous detection against a sample of the chopping frequency derived from detector 42 to derive a synchronously detected beam power signal which is fed to one input of a divider 44 for division of the sample absorption signal also fed to the divider 44 from the sample signal synchronous detector 41. The output of the divider 44 is a sample absorption signal normalized to the beam power which can vary from one wavelength to another depending upon the wavelength selected as determined by a laser wavelength selector 45 which controls the setting of the grating 13 via a suitable mechanical linkage. This normalized absorption signal is fed to one input of a recorder 46 for recording as a function of the selected laser wavelength which is also fed to the recorder 46 from laser wavelength selector 45. Thus, the recorder 46 records the absorption data as a function of the laser wavelength to derive an absorption spectrum of the fluid sample under analysis.

The absorption of the fluid sample under analysis as a function of the perturbing energy is derived by modulating the source 36 of perturbing energy, such as ultraviolet radiation, at first and second modulation frequencies $f_2$ and $f_3$ as determined by modulators 38 and 39, respectively. The normalized absorption signal derived from the output of divider 44 is fed to one input of a synchronous detector 47 for synchronous detection against a reference signal at modulation frequency $f_2$ derived from modulator 38 to derive a synchronously detected output signal corresponding to the change in absorption due to the presence of the ultraviolet or perturbing energy. This signal is thence fed to the recorder 46 for recording as a function of time or wavelength.

A sample of the intensity modulation or sweep signal $f_3$ is fed to one input of a recorder 48 for controlling the X axis of an X-Y recorder, whereas the detected absorption signal from the output of synchronous detector 47 is fed to the Y input of the recorder 48 for recording the perturbed absorption signal as a function of the intensity of the perturbing energy so that threshold effects are readily detected.

Transient absorption effects of the fluid under analysis are readily detected by feeding an output of the pulse modulator 38 to the input trigger terminal of an oscilliscope 49 which serves to trigger the horizontal sweep and the normalized absorption signal is fed to the vertical input of the oscilliscope 49 so that the absorption signal following each pulse of the pulse modulator 38 is displayed. In this manner transient absorption effects are readily detected and recorded by photographing the oscilliscope 49.

A heater 51 is disposed in heat exchanging relation with the catalytic surface 32 for controlling the temperature thereof. The heater 51 is energized with heating current from the output of a temperature sweep controller 52 which sweeps the temperature 51 at a sweep frequency $f_5$ less than $f_1$. An output of the sweep frequency $f_5$ is fed to the X input of an X-Y recorder 53 for recording as a function of the normalized absorption signal fed to the Y terminal as derived from the output of divider 44, whereby an X-Y plot of catalyst temperature vs. absorption signal is derived in order to ascertain temperature effects of the catalyst on the fluid-catalyst interaction process and/or reaction products.

Reactions and reaction products between two or more constituents of the fluid medium are monitored by injecting a reactant sample B from a source 55 via an injector 56 into the fluid medium fed into the cell 17. The reactant sample B is fed in at a modulation frequency $f_4$ as determined by a modulator 57. The normalized absorption signal at the output of divider 44 is fed to one input of a synchronous detector 58 for synchronous detection against a sample of the modulation frequency $f_4$ to derive an output corresponding to the absorption of the sample B constituent and/or the reaction products with sample A. The output of synchronous detector 58 is fed to one input of the recorder 46 for recording as a function of laser wavelength. In addition, the sample B injector modulation frequency signal $f_4$ is fed to one input of the trigger of an oscilliscope 61 for triggering the horizontal sweep thereof, whereas a sample of the normalized absorption signal, as derived from the output of the divider 44, is fed to the vertical terminal of the oscilliscope for display and/or recording as a function of time so that the transient effects of the introduction of the sample constituent B into the fluid medium containing sample constituent A or its reaction with the catalyst is detected and recorded. If the reaction times are so short that sample B totally reacts or substantially totally reacts in the fluid conduit 24 leading to the cell 17, the source 55 of sample material B may be injected directly into the cell 17 via source 62 and injector 63, as controlled from another output of the injector modulator 57. As an alternative to the recorders and oscilliscopes of FIG. 1 these may be replaced by a digital computer 60 which internally generates all the modulation and sweep frequencies and detects the resultant absorption signals, analyzing, recording and displaying same.

Referring now to FIG. 2, there is shown an alternative embodiment of the detector cell 17 for applying both a static and alternating electric field E to the fluid medium in the path of the laser beam 12. In this embodiment, a pair of electrodes 65 and 66 are disposed on opposite sides of the laser beam path 12. The electrodes are supported from the inside wall of the cell 17 via insulators 67. Electrode 65 is connected to ground, whereas electrode 66 is connected to a source of either positive or negative DC potential 68 via a modulator 69 at $f_2$, feedthrough insulator 71 and lead 72. Also, a source 73 of AC electrical potential is coupled to electrode 66, whereby positive or negative DC electric field and/or an alternating electric field is impressed on the fluid medium in the region of the laser beam 12. The DC electric field may be utilized for polarizing electrically polar molecules of the sample fluid or it may be utilized for creating a silent electrical discharge in the fluid medium of the cell. Such a silent discharge serves to produce displacement electrical currents in the cell 17 which can give rise to molecular dissociation and recombination. In addition, in the presence of certain types of fluid sample constituents such as oxygen, the electrical discharge can produce ozone which can react with the other molecular or atomic constituents of the fluid under analysis. By modulating the silent discharge, via a modulator 69 at $f_2$, the various transient effects can be observed on scope 49 and by sweeping the intensity of the discharge, threshold effects can be observed on recorder 48.

Referring now to FIG. 3, there is shown an alternative sample cell 17 incorporating features of the present invention. In cell 17 of FIG. 3, electric coils 74 are wound in magnetic field aiding relation so as to produce, when energized with current, a magnetic field H in the fluid medium in the region of the laser beam path 12. The coils 74 are energized with dc current from a source 75 of dc current, such current being modulated at $f_2$ via modulator 38. Also, the coils 74 are energized with ac current derived from a source 76 of ac current and subject to modulation by modulator 38 at modulation frequency $f_2$. The dc magnetic field may be utilized for polarizing magnetic constituents such as ozone, and/or the alternating magnetic field may be utilized for establishing an electrical discharge in the fluid medium in a manner similar to that described with regard to the cell 17 of FIG. 2.

Referring now to FIG. 4, there is shown an alternative cell 17 of the present invention. Cell 17 is similar to that of FIG. 1 with the exception that the chamber has been extended at 78 to accomodate a piston 79 sealed to the inside wall of the cell 17 via a bellows 81. The piston 79 includes a threaded extension 82 threadably mated with a nut 83 captured against axial translation via housing 84 and ball bearing race assemblies 85. The nut 83 is driven from a motor 86 via a drive gear 87. Since the nut 83 is captured against axial translation, rotation thereof produces axial translation of the piston rod 82 and the piston 79 for effecting a sweep of the pressure of the fluid medium within the cell 17. Superimposed upon the sweep of the pressure inside the cell 17 is a dithering of that pressure produced by rotation of a cam 89 which causes a dithering of the housing 84 and thence of the piston 79. The cam 89 produces a modulation of the pressure at the modulation frequency $f_2$ and a conventional fixed sensor 92, such as magnetic pickup coil magnetically coupled to a magnet carried by the dithered piston rod 82 senses the dithering action thereof and feeds the picked up dither signal to the recorder 49 and the synchronous detector 47. The pressure sweep is also detected by a conventional detector 93 such as a potentiometer 93 which feeds its $f_3$ output to recorder 48.

Referring now to FIG. 9 there is shown in spectrum (A) at 95 the absorption spectrum for a sample fluid with no pressure broadening. From spectrum 95 it is seen that there are a number of different absorption spectral lines, some overlapping. Referring now to spectrum (B) at 96, there is shown the same spectrum as 95 only under conditions of increased sample fluid pressure relative to the pressure for spectrum 95. This spectrum shows the affects of pressure broadening on the individual resonance lines. It is seen that the three resonance lines spread into overlapping relation and lose some of their spectral detail. Referring now to waveform (C), there is shown an infrared laser source spectrum for irradiating the fluid sample with the beam of infrared radiation at three different wavelengths, $\lambda_1$, $\lambda_2$ and $\lambda_3$.

Referring now to spectrum (D) there is shown the absorption signal output for irradiation of the spectrum 95 with the infrared laser source spectrum of (C). Because the narrow laser lines $\lambda_1$, $\lambda_2$ and $\lambda_3$ coincided in wavelength with only a very weak portion of only one of the lines of absorption spectrum 95, only one very small absorption signal output is obtained at $\lambda_2$, as shown at 97. However, when the same fluid sample medium is pressure broadened as indicated in waveform 96, the absorption signal output for the three wavelengths $\lambda_1$, $\lambda_2$ and $\lambda_3$ is increased substantially as indicated at 98, 99 and 101. In addition, modulation of the fluid sample pressure at the modulation frequency $f_2$ will yield information corresponding to the slope of the pressure broadened spectrum at the points of coincidence at the irradiating laser lines at $\lambda_1$, $\lambda_2$ and $\lambda_3$. Thus the modulation superimposed upon a linear sweep of the pressure in the cell 17 allows recording of the first derivative of the absorption spectrum.

Referring now to FIG. 5, there is shown an alternative absorption detection cell 17 wherein the fluid medium, in the region of the laser beam 12, and/or the catalyst surface 32 is irradiated with a beam of electrons 103. The electrons are derived from a high energy accelerator 104 such as a linear accelerator and passed through an electron permeable wall 105 separating the accelerator 104 from the cell 17. The current and voltage of the electron beam can be swept and these parameters of the electron beam may be modulated by modulator 38 and swept by sweeper 39. The beam of electrons 103 serves to vary the electron density and/or ionization fluid medium and to produce effects in the catalyst 32 which in turn interacts with the fluid medium.

Referring now to FIG. 6 there is shown an alternative sample absorption detector cell 17 wherein the temperature of the cell 17 and fluid medium is swept or controlled. More particularly, the fluid conduit 24 passes through a heat exchanger 106 which is controlled by the output of a temperature sweep or controller 107 for either heating or cooling the fluid medium passing into the cell 17. In addition, the temperature sweep 107 controls the temperature of the oven 31. The output of the temperature sweep 107 is fed to one input of the recorder 53 for recording as a function of the normalized absorption signal derived from the output of the divider 44.

Referring now to FIG. 7 there is shown an alternative sample cell 17 similar to that of FIG. 5 with the exception that the fluid medium and/or the catalytic surface 32 is irradiated by X- or γ-ray radiation derived from a target 109 bombarded by a high energy electron beam derived from electron accelerator 104. The γ- or X-rays pass through a γ- or X-ray permeable window 110 into the cell 17. As in the case of the ultraviolet radiation of FIG. 1, the γ- or X-ray radiation may be modulated in intensity at modulation frequency $f_2$ and swept in intensity by sweep signal $f_3$.

Referring now to FIG. 8, there is shown an alternative fluid sample absorption detector cell 17 incorporating features of the present invention. In the cell of FIG. 8, an ultrasonic transducer 111 is disposed opposite the catalytic surface 32 for irradiating the catalytic surface with ultrasonic waves for dislodging and otherwise perturbing the interaction of the surface 32 with the fluid under analysis. The ultrasonic waves are modulated in frequency at $f_2$ and swept in intensity at $f_3$ in the manner as previously described with regard to FIG. 1. The normalized absorption signal is displayed and recorded in the manner as previously described with regard to FIG. 1 for observing the transient response after each pulse of the ultrasonic energy and as a function of the swept intensity of the ultrasonic energy for determining theshold effects.

The laser absorption spectrometer system 11 is useful for providing information concerning the electric and magnetic polarity for constituents of the fluid under analysis, dissociation rates of the sample constituents, recombination rates of the sample constituents, transient molecular species of the fluid including reactants and reaction products, catalytic behavior and mechanisms, suppression of interferring molecular species, and enhanced detection of selected molecular species.

An important consideration in the spectrometer system 11, particularly in the application of the perturbing energy, is the ability to program (sweep) the perturbing energy density and the time dependence thereof. In the case of a sweep of the energy density, threshold effects can be ascertained and the time dependence allows use of synchronous detectors, including phase detectors, lock-in amplifiers or box car integrators, referenced against the acoustic signal at the output of divider 44 to yield high signal-to-noise ratio especially where transient effects are taking place.

What is claimed is:

1. In a method of laser absorption spectroscopy, the steps of:
   irradiating a fluid sample medium with a beam of coherent infrared optical radiation;
   coupling a detector in energy exchanging relation with the fluid sample medium to detect the absorption of energy by the fluid medium from the beam of coherent infrared optical radiation;
   changing an electrical field in the fluid medium to effect a corresponding change in the absorption of energy by the fluid medium from the beam of infrared radiation; and
   detecting resultant changes in the absorption of the infrared radiation by the fluid medium occasioned by the change in the electric field.

2. In a method of laser absorption spectroscopy, the steps of:
   irradiating a fluid sample medium with a beam of coherent infrared optical radiation;
   coupling a detector in energy exchanging relation with the fluid sample medium to detect the absorption of energy by the fluid medium from the beam of coherent infrared optical radiation;
   changing a magnetic field in the fluid medium to effect a corresponding change in the absorption of energy by the fluid medium from the beam of infrared radiation; and
   detecting resultant changes in the absorption of the infrared radiation by the fluid medium occasioned by the change in the magnetic field.

3. In a method of laser absorption spectroscopy, the steps of:
   irradiating a fluid sample medium with a beam of coherent infrared optical radiation;
   coupling a detector in energy exchanging relation with the fluid medium to detect the absorption of energy by the fluid medium from the beam of coherent infrared optical radiation;
   changing a physical or chemical parameter effecting absorption of energy by the fluid medium from the beam of infrared radiation at a first rate and a second rate, said second rate being higher than said first rate, and detecting the resultant changes in the absorption of the energy by the sample fluid medium from the beam of coherent infrared radiation at said second rate.

4. The method of claim 3 including the step of, detecting the resultant changes of the absorption of the energy by the fluid medium from the beam at the first rate.

5. In a method of laser absorption spectroscopy, the steps of:
   irradiating a fluid sample medium with a beam of coherent infrared optical radiation;
   coupling a detector in energy exchanging relation with the fluid sample medium to detect the absorption of energy by the fluid medium from the beam of coherent infrared optical radiation;
   adjusting the pressure of the fluid medium so as to effect a substantial pressure broadening of the fluid sample infrared absorption spectrum;
   changing a physical or chemical parameter effecting absorption of energy by the fluid medium by modulating the pressure of the fluid medium; and
   synchronously detecting the changes in the absorption of the energy of the fluid medium at the pressure modulation frequency or harmonics thereof.

6. In a laser absorption spectrometer:
   means for irradiating a fluid sample medium with a beam of coherent infrared optical radiation;
   detector means coupled in energy exchanging relation with the fluid sample medium to detect absorption of energy by the fluid medium from the beam of coherent infrared optical radiation;
   means for changing an electric field in the fluid medium to effect a change in the absorption of energy by the fluid medium from the beam of infrared radiation; and
   means for detecting resultant changes in the absorption of the energy by the fluid medium occasioned by said change in said electric field.

7. In a laser absorption spectrometer:
   means for irradiating a fluid sample medium with a beam of coherent infrared optical radiation;
   detector means coupled in energy exchanging relation with the fluid sample medium to detect absorption of energy by the fluid medium from the beam of coherent infrared optical radiation;
   means for changing a magnetic field in the fluid medium to effect a change in the absorption of energy by the fluid medium from the beam of infrared radiation; and
   means for detecting resultant changes in the absorption of the energy by the fluid medium occasioned by said change in said magnetic field.

8. In a laser absorption spectrometer:
   means for irradiating a fluid sample medium with a beam of coherent infrared optical radiation;
   detector means coupled in energy exchanging relation with the fluid sample medium to detect absorption of energy by the fluid medium from the beam of coherent infrared optical radiation;
   means for changing a physical or chemical parameter effecting absorption of the energy by the fluid medium from the beam at a first and second rate, said second rate being higher than said first rate; and
   means for detecting changes in absorption of the energy by the fluid medium at said second rate occasioned by the change in the physical or chemical parameter at said second rate.

9. The apparatus of claim 8 including, means for detecting the resultant changes in the absorption of energy by the fluid medium from the beam at said first rate.

10. In a laser absorption spectrometer:
    means for irradiating a fluid sample medium with a beam of coherent optical infrared radiation;
    detector means coupled in energy exchanging relation with the fluid sample medium to detect absorption of energy by the fluid medium from the beam of coherent optical infrared radiation;
    means for adjusting the pressure of the fluid medium so as to effect a substantial pressure broadening of the fluid sample infrared absorption spectrum;
    means for modulating the pressure of the fluid medium; and
    means for detecting resultant changes in the absorption of the energy by the fluid medium occasioned by the modulation of the pressure by synchronously detecting the changes in the absorption of energy by the fluid medium from the beam of infrared radiation at the pressure modulation frequency or harmonics thereof.

* * * * *